United States Patent [19]
Smith

[11] 4,327,113
[45] Apr. 27, 1982

[54] ALKANOLAMINE DERIVATIVES

[75] Inventor: Leslie H. Smith, Macclesfield, England

[73] Assignee: Imperial Chemical Industries Limited, London, England

[21] Appl. No.: 215,873

[22] Filed: Dec. 12, 1980

Related U.S. Application Data

[62] Division of Ser. No. 123,926, Feb. 22, 1980, Pat. No. 4,260,632, which is a division of Ser. No. 15,411, Feb. 26, 1979, Pat. No. 4,221,807, which is a division of Ser. No. 787,375, Apr. 14, 1977, Pat. No. 4,141,987, which is a division of Ser. No. 582,883, Jun. 2, 1975, Pat. No. 4,034,106.

[30] Foreign Application Priority Data

Jun. 5, 1974 [GB] United Kingdom ............... 24837/74

[51] Int. Cl.³ .................... A61K 31/18; C07C 143/78

[52] U.S. Cl. ............................... 424/321; 260/465 D; 260/465 E; 564/47; 564/49; 564/56; 564/82; 564/85; 564/86; 564/87

[58] Field of Search ...................... 260/465 D, 465 E; 424/321; 564/47, 49, 56, 82, 85, 86, 87

[56] References Cited

U.S. PATENT DOCUMENTS 3,928,412 12/1975 Smith ............................. 260/465 D

*Primary Examiner*—Richard Raymond
*Attorney, Agent, or Firm*—Cushman, Darby & Cushman

[57] ABSTRACT

Novel 1-heterocyclyloxy- or 1-aryloxy-3-amidoalkylamino-2-propanol derivatives, processes for their manufacture, pharmaceutical compositions containing them and methods of using them in the treatment of heart diseases. The compounds possess β-adrenergic blocking activity. Representative of the compounds disclosed is 1-(4-indolyloxy)-3-β-isobutyramidoethylamino-2-propanol.

9 Claims, No Drawings

ALKANOLAMINE DERIVATIVES

This application is a division of U.S. application Ser. No. 123,926, filed Feb. 22, 1980, now U.S. Pat. No. 4,260,632, said Ser. No. 123,926 being a divisional of Ser. No. 015,411, filed Feb. 26, 1979, now U.S. Pat. No. 4,221,807, a divisional of Ser. No. 787,375, filed Apr. 14, 1977, now U.S. Pat. No. 4,141,987, a divisional of Ser. No. 582,883, filed June 2, 1975, now U.S. Pat. No. 4,034,106.

This invention relates to new alkanolamine derivatives which possess β-adrenergic blocking activity.

According to the invention there is provided a new alkanolamine derivative of the formula

R—OCH$_2$.CHOH.CH$_2$NH—A—NH—X—Y—R$^1$ wherein A stands for an alkylene radical of from 2 to 12 carbon atoms; wherein X stands for the carbonyl (—CO—) or sulphonyl (—SO$_2$—) radical; wherein Y stands for a direct link, or for an alkylene, oxyalkylene or alkyleneoxy radical each of up to 6 carbon atoms, or for the imino (—NH—) radical, or for an alkylimino, iminoalkylene, iminoalkyleneoxy or iminoalkylenecarbonyloxy radical each of up to 6 carbon atoms, or (except when R$^1$ stands for the hydrogen atom) for the oxygen atom; and wherein either (a) R stands for a heterocyclic radical or for an aryl radical of the formula

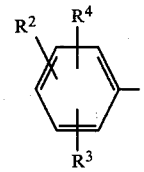

and R$^1$ stands for a heterocyclic radical or for an aryl radical of the formula:

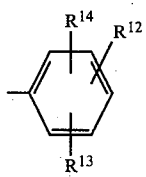

wherein R$^2$, R$^3$, R$^{12}$ and R$^{13}$, which may be the same or different, each stands for a hydrogen or halogen atom, a hydroxy, amino, nitro or cyano radical, an alkyl, hydroxyalkyl, cycloalkyl, alkenyl, alkynyl, alkoxy, alkylthio, cycloalkoxy, alkenyloxy, alkynyloxy or alkanoyl radical each of up to 6 carbon atoms, or an aryl, aryloxy or dialkylamino radical each of up to 12 carbon atoms; or wherein R$^2$ and R$^3$ together, and/or R$^{12}$ and R$^{13}$ together, form the trimethylene, tetramethylene, 1-oxotetramethylene, propenylene, but-2-enylene or buta-1,3-dienylene radical such that together with two adjacent carbon atoms of the benzene ring they form respectively the indanyl, 5,6,7,8-tetrahydronaphthyl, 5-oxo-5,6,7,8-tetrahydronaphthyl, indenyl, 5,8-dihydronaphthyl or naphthyl radical; wherein R$^4$ stands for the hydrogen atom or for an amidic radical of the formula:

R$^{15}$R$^{16}$N—CO—Q—

R$^{15}$R$^{16}$N—CO—NH—Q—

R$^{15}$R$^{16}$N—CO—Q$^1$—O— or

R$^{16}$—X—NR$^{15}$—Q— wherein Q stands for a direct link or for an alkylene or alkenylene radical each of up to 6 carbon atoms; wherein Q$^1$ stands for an alkylene radical of up to 6 carbon atoms; wherein R$^{15}$ stands for the hydrogen atom or for an alkyl radical of up to 6 carbon atoms; wherein R$^{16}$ stands for the hydrogen atom, or for an alkenyl, cycloalkyl, hydroxyalkyl or alkoxyalkyl radical each of up to 6 carbon atoms, or for an alkyl, aryl, aralkyl or aralkenyl radical each of up to 10 carbon atoms; and wherein R$^{14}$ stands for an amidic radical as defined above for R$^4$; or (b) R stands for a heterocyclic radical and R$^1$ stands for the hydrogen atom or for an alkyl, halogenoalkyl, alkenyl or cycloalkyl radical each of up to 10 carbon atoms, or for an aryl radical of the formula:

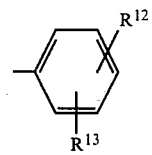

wherein R$^{12}$ and R$^{13}$, which may be the same or different, have the meanings stated above; or an acid-addition salt thereof.

It will be observed that the alkanolamine derivative of the invention possesses an asymmetric carbon atom, namely the carbon atom of the —CHOH— group in the alkanolamine side-chain, and it can therefore exist in racemic and optically-active forms. It is to be understood that this invention encompasses the racemic form of the alkanolamine derivative and any optically-active form which possesses β-adrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the "S" absolute configuration of the said —CHOH— group.

A suitable value for the alkylene radical A is, for example, the ethylene, trimethylene, tetramethylene, hexamethylene, dodecamethylene, 1-methylethylene, 2-methylethylene or 1,1-dimethylethylene radical. A is preferably the ethylene, 1-methylethylene or 1 1-dimethylethylene radical.

A suitable value for Y when it stands for an alkylene, oxyalkylene or alkyleneoxy radical is, for example, the methylene, ethylene, oxymethylene, methyleneoxy, ethyleneoxy, trimethyleneoxy, 1-methylethylideneoxy or 1-methylpropylideneoxy radical.

A suitable value for Y when it stands for an alkylimino, iminoalkylene, iminoalkyleneoxy or iminoalkylenecarbonyloxy radical is, for example, the methylimino, iminomethylene, iminomethyleneoxy or iminomethylenecarbonyloxy radical.

Y is preferably a direct link or the methylene, methyleneoxy or imino radical.

A suitable value for R or $R^1$ when it stands for a heterocyclic radical is, for example, a mono-, bi- or tricyclic heterocyclic radical in which at least one ring is a 5 or 6-membered saturated or unsaturated hetero-ring containing one, two or three heteroatoms selected from nitrogen, oxygen and sulphur atoms; and in which the second and/or third ring, if present, may be a hetero-ring as defined above or may be a benzene ring; and which heterocyclic radical may optionally contain one or more substituents selected from halogen atoms, for example chlorine and bromine atoms, alkyl, alkoxy, acylamino, carbamoyl and alkanoyl radicals each of up to 6 carbon atoms, for example methyl, ethyl, methoxy, ethoxy, acetamido, methylcarbamoyl and acetyl radicals, aryl and aryloxy radicals each of up to 10 carbon atoms, for example phenyl, p-chlorophenyl and phenoxy radicals, and amino and substituted amino radicals, for example amino, alkylamino, dialkylamino and heterocyclic amino radicals each of up to 6 carbon atoms, for example amino, methylamino, dimethylamino and morpholino radicals, and, where the heterocyclic radical bears an appropriate degree of saturation, which heterocyclic radical may optionally bear one or two oxo substituents.

A particular heterocyclic radical is, for example, a pyrrolyl, furyl, thienyl, imidazolyl, pyrazolyl, oxazolyl, isoxazolyl, thiazolyl, thiadiazolyl, pyridyl, pyranyl, pyrazinyl, pyridazinyl, pyrimidinyl, indolyl, isoindolyl, benzofuranyl, benzothienyl, benzimidazolyl, benzothiazolyl, benzothiadiazolyl, quinolyl, chromanyl, chromenyl, thiochromanyl, benzodioxanyl, carbazolyl or phenothiazinyl radical, for example the 2-pyrrolyl, 2-furyl, 2-thienyl, 3-thienyl, 2-imidazolyl, 5-methyl-3-pyrazolyl, 2-phenyl-5-methyl-3-pyrazolyl, 2-oxazolyl, 3-isoxazolyl, 2-thiazolyl, 2-p-chlorophenyl-4-thiazolyl, 4-morpholino-1,2,5-thiadiazol-3-yl, 4-pyridyl, 2-methyl-4-oxo-4H-pyran-3-yl, 3-methyl-2-pyrazinyl, 3-phenyl-2-pyrazinyl, 2-pyridazinyl, 2-p-chlorophenyl-6-methoxypyrimidin-4-yl, 2-indolyl, 3-indolyl, 4-indolyl, 2-methylindol-4-yl, 2,3-dihydro-2-oxo-4-indolyl, 3-oxo-2-phenyl-3H-isoindol-1-yl, 4-benzo[b]furanyl, 2,3-dimethyl-4-benzo[b]furanyl, 2-acetyl-7-benzo[b]furanyl, 4-benzothienyl, 2-benzimidazolyl, 5-benzothiazolyl, 5-(benzo[c]-[1,2,5]thiadiazolyl), 2-quinolyl, 1,2-dihydro-2-oxo-5-quinolinyl, 1,4-dihydro-6-methoxy-4-oxo-2-quinolinyl, 1,2,3,4-tetrahydro-2-oxo-5-quinolinyl, 4-oxochroman-8-yl, 4-methyl-2-oxo-2H-chromen-8-yl, thiochroman-8-yl, 1,4-benzodioxan-5-yl, 1-carbazolyl or 1-phenothiazinyl radical.

A suitable value for $R^1$ when it stands for an alkyl, halogenoalkyl, alkenyl or cycloalkyl radical is, for example, the methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, hydroxyalkyl, cycloalkyl, alkenyl, alkynyl, alkoxy, alkylthio, cycloalkoxy, alkenyloxy, alkynyloxy or alkanoyl radical is, for example, the methyl, ethyl, n-propyl, hydroxymethyl, 1-hydroxyethyl, cyclopropyl, cyclopentyl, allyl, ethynyl, methoxy, isopropoxy, methylthio, cyclopentyloxy, allyloxy, propargyloxy, formyl or acetyl radical.

A suitable value for $R^2$, $R^3$, $R^{12}$ or $R^{13}$ when it stands for an aryl, aryloxy, aralkoxy or dialkylamino radical is, for example, the phenyl, phenoxy or dimethylamino radical.

A suitable value for Q or $Q^1$ when it stands for an alkylene radical is, for example, the methylene, ethylene, trimethylene, ethylidene or 1-methylethylene radical. A suitable value for Q when it stands for an alkenylene radical is, for example, the vinylene radical.

A suitable value for $R^{15}$ when it stands for an alkyl radical is, for example, the methyl radical.

A suitable value for $R^{16}$ is, for example, the hydrogen atom or the allyl, cyclopropyl, cyclopentyl, cyclohexyl, 2-hydroxyethyl, 3-hydroxypropyl, 2-hydroxy-1-methylethyl, 2-hydroxy-1,1-dimethylethyl, β-methoxyethyl, methyl, ethyl, n-propyl, isopropyl, n-butyl, t-butyl, n-pentyl, n-hexyl, n-nonyl, phenyl, p-tolyl, p-chlorophenyl, benzyl or styryl radical.

A particular value for $R^{14}$, or for $R^4$ when it stands for an amidic radical is, for example, the acetamido, propionamido, methanesulphonamido, carbamoyl, carbamoylmethyl, acetamidomethyl, 3-methylureido, 3-n-butylureido, carbamoylmethoxy, N-methylcarbamoylmethoxy or N-β-hydroxyethylcarbamoylmethoxy radical. The substituent $R^4$ when present is preferably in the ortho-position of the benzene ring, and the substituent $R^{14}$ is preferably in the para-position of the benzene ring.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), of a salt derived from an acidic synthetic resin, for example a sulphonated polystyrene resin.

One preferred alkanolamine derivative of the invention is a compound of the formula given above wherein A stands for the ethylene, 1-methylethylene or 1,1-dimethylethylene radical, wherein R stands for an aryl radical, wherein $R^1$ stands for a monocyclic, 5- or 6-membered, fully-unsaturated heterocylic radical which contains one nitrogen, oxygen or sulphur atom as heteroatom, wherein $R^2$, $R^3$ and $R^4$ all stand for hydrogen, wherein X stands for the carbonyl radical and wherein Y stands for a direct link, or an acid-addition salt thereof.

A second preferred alkanolamine derivative of the invention is a compound of the formula given above wherein A stands for the ethylene, 1-methylethylene or 1,1-dimethylethylene radical, wherein R and $R^1$ both stand for aryl radicals, wherein $R^2$ stands for hydrogen or for a chloro, cyano, nitro or methoxy radical which is in the 2-position of the aryl nucleus, wherein $R^3$, $R^4$, $R^{12}$ and $R^{13}$ all stand for hydrogen, wherein $R^{14}$ stands for a radical of the formula:

$R^{16}NCO-Q-$ $R^{16}NHCONH-$ $R^{16}NHCO-Q^1-O-$ or $R^{16}-X-NH-Q-$ wherein $R^{16}$ stands for hydrogen or for the methyl radical, wherein Q stands for a direct link or for the methylene radical, and wherein $Q^1$ stands for the methylene radical, which radical $R^{14}$ is in the 4-position of the aryl nucleus, wherein X stands for the carbonyl or sulphonyl radical and wherein Y stands for a direct link or for the methylene or methyleneoxy radical, or an acid-addition salt thereof.

A third preferred alkanolamine derivative of the invention is a compound of the formula given above wherein A stands for the ethylene, 1-methylethylene or 1,1-dimethylethylene radical, wherein R stands for an aryl radical, wherein $R^1$ stands for a heterocyclic radical, wherein $R^2$ stands for hydrogen or for a chloro or cyano radical which is in the 2-position of the aryl nucleus, wherein $R^3$ and $R^4$ both stand for hydrogen, wherein X stands for the carbonyl radical and wherein Y stands for the methylene radical, or an acid-addition salt thereof.

A fourth preferred alkanolamine derivative of the invention is a compound of the formula given above wherein A stands for the ethylene, 1-methylethylene or 1,1-dimethylethylene radical, wherein R stands for a heterocyclic radical, wherein $R^1$ stands for an aryl radical or for an alkyl radical of up to 10 carbon atoms, wherein $R^{12}$ stands for hydrogen or for a nitro, amino, hydroxy or acetyl radical, wherein $R^{13}$ stands for hydrogen, wherein $R^{14}$ if present, has the meaning stated in the last but one paragraph in respect of the second preferred alkanolamine derivative of the invention, wherein X stands for the carbonyl radical and wherein Y stands for a direct link, or for the imino, methylene or methyleneoxy radical, or an acid-addition salt thereof. The heterocyclic radical R is preferably the 4-indolyl, 4-benzo[b]furanyl, 4-benzothienyl, 4-morpholino-1,2,5-thiadiazol-3-yl, 2-thiazolyl or 1,4-benzodioxan-5-yl radical.

Specific alkanolamine derivatives of the invention are those hereinafter described in the Examples. Of these, preferred compounds by virtue of their high cardioselective β-adrenergic blocking activity (as hereinafter defined) are:

1-phenoxy-3-β-isonicotinamidoethylamino-2-propanol;
1-phenoxy-3-(β-2-thenamidoethyl)amino-2-propanol;
1-phenoxy-3-(β-2-furamidoethyl)amino-2-propanol;
1-phenoxy-3-β-(p-acetamidobenzenesulphonamido)ethylamino-2-propanol;
1-phenoxy-3-β-(p-acetamidobenzamido)ethylamino-2-propanol;
1-(2-nitrophenoxy)-3-β-(p-acetamidophenylacetamido)ethylamino-2-propanol;
1-(2-methoxyphenoxy)-3-β-(p-acetamidophenylacetamido)ethylamino-2-propanol;
1-(2-chlorophenoxy)-3-β-(p-acetamidophenylacetamido)ethylamino-2-propanol;
1-(2-cyanophenoxy)-3-β-(p-methanesulphonamidophenylacetamido)-ethylamino-2-propanol;
1-(2-cyanophenoxy)-3-β-(p-acetamidomethylphenoxyacetamido)ethylamino-2-propanol;
1-(2-cyanophenoxy)-3-β-(p-carbamoylmethoxyphenylacetamido)ethylamino-2-propanol;
1-(2-cyanophenoxy)-3-β-(3-thienylacetamido)ethylamino-2-propanol;
1-(2-chlorophenoxy)-3-β-(2-benzimidazolylacetamido)ethylamino-2-propanol;
1-(2-cyanophenoxy)-3-β-(1,4-dihydro-6-methoxy-4-oxoquinolin-2-ylacetamido)ethylamino-2-propanol;
1-(4-indolyloxy)-3-β-isobutyramidoethylamino-2-propanol;
1-(2-thiazolyloxy)-3-β-isobutyramidoethylamino-2-propanol;
1-(4-morpholino-1,2,5-thiadiazol-3-yloxy)-3-β-isobutyramidoethylamino-2-propanol;
1-(1,4-benzodioxan-5-yl)-3-(1-methyl-2-phenylacetamidoethyl)-amino-2-propanol; and
1-(1,4-benzodioxan-5-yl)-3-β-(p-3-methylureidophenylacetamido)-ethylamino-2-propanol
and the acid-addition salts thereof.

The alkanolamine derivative of the invention may be manufactured by any chemical process known to be useful for the manufacture of chemically-analogous compounds.

According to a further feature of the invention there is provided a process for the manufacture of the alkanolamine derivative of the invention which comprises assembling in sequence, by chemical synthesis, the five radicals:

(i) an aryloxy radical of the formula:

R—O— wherein R has the meaning stated above;

(ii) an oxygenated three carbon radical of the formula:

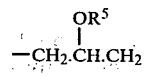

wherein $R^5$ stands for hydrogen or for a protecting group;

(iii) an imino radical of the formula —$NR^6$—, wherein $R^6$ stands for hydrogen or for a protecting group;

(iv) a radical of the formula:

—A—$NR^7$— wherein A has the meaning stated above and wherein $R^7$ stands for hydrogen or for a protecting group; and (v) a radical of the formula:

—X—Y—$R^1$ wherein $R^1$, X and Y have the meanings stated above; whereafter if one or more of $R^5$, $R^6$ and $R^7$ stands for a protecting group, the one or more protecting groups are removed.

The various stages of the assembly may be carried out in any possible order. Thus, for example:

(a) a phenolic compound of the formula:

R—OH wherein R has the meaning stated above, may first be reacted with an oxygenated three-carbon derivative, for example a compound of the formula:

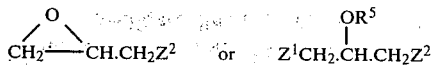

wherein $R^5$ has the meaning stated above, wherein $Z^1$ stands for a displaceable radical and wherein $Z^2$ stands for the hydroxy radical or for a displaceable radical. If $Z^2$ stands for the hydroxy radical, the intermediate compound obtained is further reacted with a reagent which will replace the primary hydroxy radical $Z^2$ with a displaceable radical $Z^1$. The resulting product, which is a compound of the formula:

$$R-OCH_2Z^3$$

wherein R has the meaning stated above and wherein $Z^3$ stands for the group $$-\overset{O}{\overset{\diagup\diagdown}{CH-CH_2}}$$

or the group $$-\overset{OR^5}{\underset{|}{CH}}.CH_2Z^1,$$

wherein $R^5$ and $Z^1$ have the meanings stated above, or which may be, when $R^5$ stands for hydrogen, a mixture of such compounds wherein $Z^3$ has both meanings stated above, is then reacted with an amine of the formula:

$$HNR^6-A-NR^7-X-Y-R^1$$

wherein A, $R^1$, $R^6$, $R^7$, X and Y have the meanings stated above, or with a precursor of such an amine.

(b) An oxygenated three-carbon derivative, for example a compound of the formula:

$$\overset{O}{\overset{\diagup\diagdown}{CH_2-CH.CH_2Z^2}} \quad \text{or} \quad Z^1CH_2.\overset{OR^5}{\underset{|}{CH}}.CH_2Z^2$$

wherein $R^5$, $Z^1$ and $Z^2$ have the meanings stated above, is reacted with an amine of the formula:

$$HNR^6-A-NR^7-X-Y-R^1$$

wherein A, $R^1$, $R^6$, $R^7$, X and Y have the meanings stated above, or with a precursor of such an amine. If $Z^2$ stands for the hydroxy radical the intermediate compound obtained is further reacted with a reagent which will replace the primary hydroxy radical $Z^2$ with a displaceable radical $Z^1$. The resulting product, which is a compound of the formula:

$$Z^3CH_2-NR^6-A-NR^7-X-Y-R^1$$

wherein A, $R^1$, $R^6$, $R^7$, X, Y and $Z^3$ have the meanings stated above, or which may be, when $R^5$ stands for hydrogen, a mixture of such compounds wherein $Z^3$ has both meanings stated above, is then reacted with a phenolic compound of the formula:

$$R-OH$$

wherein R has the meaning stated above.

Alternatively, the compound of the formula:

$$Z^1CH_2.\overset{OR^5}{\underset{|}{CH}}.CH_2-NR^6-A-NR^7-X-Y-R^1$$

may be converted, by heating, into the azetidinol derivative of the formula:

$$\begin{array}{c} R^5OCH-CH_2 \\ | \quad\quad\quad | \\ CH_2-NR^6-A-NR^7-X-Y-R^1 \\ \oplus \quad\quad\quad\quad Z^1 \ominus \end{array}$$

When $R^6$ stands for hydrogen, the azetidinol salt is converted into its free base form and then reacted with a phenolic compound of the formula stated above. When $R^6$ stands for a protecting group, the azetidinium salt is reacted directly with the said phenolic compound. The azetidinol derivative may alternatively be obtained by the reaction of a compound of the formula:

$$Z^1CH_2.\overset{OR^5}{\underset{|}{CH}}.CH_2Z^1$$

wherein $R^5$ and $Z^1$ have the meanings stated above, with an amine of the formula:

$$HNR^6-A-NR^7-X-Y-R^1$$

wherein A, $R^1$, $R^6$, $R^7$, X and Y have the meanings stated above.

A suitable value for $Z^1$, or for $Z^2$ when it stands for a displaceable radical, is, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

A suitable reagent which will replace the primary hydroxy radical $Z^2$ with a displaceable radical $Z^1$ is, for example, a halogenating agent, for example a thionyl halide, for example thionyl chloride or thionyl bromide, or a sulphonylating agent, for example an alkanesulphonyl halide or an arenesulphonyl halide, for example methanesulphonyl chloride, benzenesulphonyl chloride or toluene-p-sulphonyl chloride.

The reaction involving a phenolic reactant may be carried out in the presence of an acid-binding agent, for example an alkali metal hydroxide, for example sodium hydroxide, or an organic base, for example piperidine. Alternatively, an alkali metal derivative of the phenolic reactant, for example the sodium or potassium derivative, may be used as starting material. The reaction may be carried out in a diluent or solvent, for example methanol or ethanol, and it may be accelerated or completed by the application of heat, for example by heating to the boiling point of the diluent or solvent.

The reaction involving an amine of the formula:

$$HNR^6-A-NR^7-X-Y-R^1$$

may be carried out at ambient temperature or it may be accelerated or completed by the application of heat, for example by heating to a temperature of 90°–110° C.; it may be carried out at atmospheric or at an elevated pressure, for example by heating in a sealed vessel; and it may be carried out in an inert diluent or solvent, for example methanol, ethanol or n-propanol, or an excess of the amine may be used as diluent or solvent.

(c) The series of reactions described under (a) or (b) above may be carried out except that an amine of the formula $R^6NH_2$ is used in place of an amine of the formula:

$$HNR^6-A-NR^7-X-Y-R^1$$

it being understood that when $R^6$ stands for hydrogen the amine is ammonia. The radical $$-A-NR^7-X-Y-R^1$$

may then be inserted as a separate step, for example either by the reaction of the final product from the series of reactions described under (a) or (b) above with a compound of the formula:

$$Z^1-A-NR^7-X-Y-R^1$$

wherein A, $R^1$, $R^7$, X, Y and $Z^1$ have the meanings stated above, or, when $R^6$ stands for hydrogen, by the reaction under reducing conditions of the final product from the series of reactions described under (a) or (b) above with a carbonyl compound of the formula:

$$A^1-CO-A^2-NR^7-X-Y-R^1$$

wherein $R^1$, $R^7$, X and Y have the meanings stated above and wherein $A^1$ stands for hydrogen or for an alkyl radical and $A^2$ stands for an alkylene radical such that the radical $$\begin{array}{c} A^1 \\ | \\ -CH-A^2- \end{array}$$

has the same meaning as is stated above for A.

The reaction involving a compound of the formula:

$$Z^1-A-NR^7-X-Y-R^1$$

may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, in an inert diluent or solvent, for example in one or more solvents selected from water, ethanol and an excess of the carbonyl compound used as starting material; or by the presence of an alkali metal borohydride, for example sodium borohydride or lithium cyanoborohydride, in an inert diluent or solvent, for example in one or more solvents selected from water, ethanol, methanol and an excess of the carbonyl compound used as starting material. It is to be understood that when in the starting material $R^1$ stands for an alkenyl radical, or one or more of $R^2$, $R^3$, $R^{12}$ and $R^{13}$ stands for a halogen atom or for a nitro, cyano, alkenyl, alkynyl, alkylthio, alkenyloxy or alkynyloxy radical, or Q stands for an alkenylene radical, or $R^{16}$ stands for an alkenyl or aralkenyl radical, hydrogen and a hydrogenation catalyst are preferably not used to provide the reducing conditions, in order to prevent the radical $R^1$, $R^2$, $R^3$, $R^{12}$, $R^{13}$, $R^{16}$ or Q from being affected by catalytic hydrogenation.

(d) The series of reactions described under (a) or (b) above may be carried out except that an amine of the formula:

$$HNR^6-A-NHR^7$$

wherein $R^6$, $R^7$ and A have the meanings stated above, is used in place of an amine of the formula:

$$NHR^6-A-NR^7-X-Y-R^1,$$

or the reaction described under (c) above may be carried out except that the radical $-A-NHR^7$ is inserted in place of the radical $-A-NR^7-X-Y-R^1$. The amidic linkage $-NR^7-X-$ may then be formed as a separate step by reaction of the resulting product, which is a compound of the formula:

$$\begin{array}{c} OR^5 \\ | \\ R.OCH_2.CH.CH_2NR^6-A-NHR^7 \end{array}$$

wherein R, $R^5$, $R^6$, $R^7$ and A have the meanings stated above, with a compound of the formula:

$$Z^4-X-Y-R^1$$

wherein $R^1$, X and Y have the meanings stated above and wherein $Z^4$ stands for a displaceable radical, or, when X stands for the carbonyl radical and Y stands for the imino radical, with an isocyanate of the formula:

$$-OCN-R^1$$

wherein $R^1$ has the meaning stated above.

A suitable value for $Z^4$ is, for example, a radical of the formula $Z^1$ defined above, or an alkoxy or aryloxy radical of up to 10 carbon atoms, for example the methoxy, ethoxy or phenoxy radical. Alternatively, $Z^4$ may be the hydroxy radical, in which case the reaction is carried out in the presence of a condensing agent, for example a carbodi-imide.

(e) A compound wherein one or more of $R^5$, $R^6$ and $R^7$ stands for a protecting group may be prepared by the series of reactions described under (a) or (b) or (c) or (d) above. Alternatively, a suitable protecting group may be introduced by conventional means into an intermediate compound at any stage preceding the final stage.

A suitable value for $R^5$ when it stands for a protecting group is, for example, a hydrogenolysable radical, for example an α-arylalkyl, α-arylalkoxy-carbonyl or α-arylalkoxymethyl radical, for example the benzyl, benzyloxycarbonyl or benzyloxymethyl radical, or an acyl radical, for example an alkanoyl radical of up to 20 carbon atoms, for example the acetyl, t-butoxycarbonyl or 2,2,2-trichloroethoxycarbonyl radical, or an aroyl radical of up to 10 carbon atoms, for example the benzoyl radical, or an α-alkoxyalkyl radical (that is, a radical which forms with the oxygenated three-carbon radical an acetal radical), for example the tetrahydropyranyl radical, or a tertiary alkyl radical, for example the t-butyl radical.

A suitable value for $R^6$ when it stands for a protecting group is, for example, a hydrogenolysable or tertiary alkyl radical as defined for $R^5$, or a relatively easily hydrolysable acyl radical, for example the 2,2,2-trichloroethoxycarbonyl or t-butoxycarbonyl radical. It is to be understood that when $R^6$ stands for an acyl radical, this radical must be removable under conditions which will not destroy the amidic linkage —$NR^7$—X or the amidic linkage which may be in the substituent $R^4$ or $R^{14}$.

Alternatively, $R^5$ and $R^6$ may be joined together so that one protecting group serves to protect both the oxygen and nitrogen atoms. Such a protecting group may be, for example, a radical of the formula —CH-$R^8$—, wherein $R^8$ stands for hydrogen, or for an alkyl radical of up to 4 carbon atoms or an aryl radical of up to 10 carbon atoms, such that it forms, together with the adjacent oxygen and nitrogen atoms and two carbon atoms of the three-carbon radical, an oxazolidine nucleus.

A suitable value for $R^7$ when it stands for a protecting group is, for example, a hydrogenolysable or tertiary alkyl group as defined for $R^5$ or $R^6$.

The hydrogenolysable protecting group $R^5$, $R^6$ or $R^7$ may be removed, for example, by catalytic hydrogenolysis, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The acyl protecting group $R^5$ or $R^6$ may be removed by hydrolysis in the presence of a base, for example an alkali metal hydroxide, in a diluent or solvent, for example water, methanol, ethanol or a mixture thereof. It is to be understood that the hydrolytic conditions used must be sufficiently mild to avoid hydrolysis of the amidic linkage —$NR^7$—X or the amidic linkage which may be present in the substituent $R^4$ or $R^{14}$.

The α-alkoxyalkyl protecting group $R^5$ or the protecting group —$R^8$—CH— formed by $R^5$ and $R^6$ taken together may be removed by hydrolysis in the presence of an acid, for example a mineral acid, for example aqueous hydrochloric acid, and the hydrolysis may be carried out at a temperature of up to 100° C.

The tertiary alkyl protecting group $R^5$, $R^6$ or $R^7$, or the acyl protecting group $R^5$ or $R^6$ when it stands for a tertiary alkoxycarbonyl radical, for example the t-butoxycarbonyl radical, may be removed by treatment with an acid, for example hydrogen chloride, in anhydrous conditions, for example in ethereal solution.

A compound wherein one or more of $R^2$, $R^3$, $R^{12}$ and $R^{13}$ stands for the hydroxy or amino radical may be obtained by the hydrogenolysis of the corresponding compound wherein one or more of $R^2$, $R^3$, $R^{12}$ and $R^{13}$ stands for, respectively, the nitro radical or an α-aryloxy radical, for example the benzyloxy radical.

One preferred process for the manufacture of the alkanolamine derivative of the invention comprises the reaction of a compound of the formula:

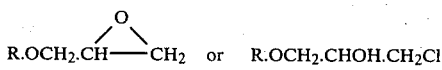

wherein R has the meaning stated above (both of which compounds may be obtained by the reaction of the corresponding phenolic compound with epichlorohydrin), with an amine of the formula $R^6$NH—A—N-H—X—Y—$R^1$ wherein A, $R^1$, X and Y have the meanings stated above and wherein $R^6$ stands for hydrogen or for the benzyl) radical, whereafter if $R^6$ stands for the benzyl radical this radical is removed by hydrogenolysis.

A second preferred process for the manufacture of the alkanolamine derivative of the invention comprises the reaction of a compound of the formula R.OCH$_2$.-CHOH.CH$_2$NH—A—NH$R^7$ wherein R and A have the meanings stated above and wherein $R^7$ stands for hydrogen or for the benzyl radical, with a compound of the formula $Z^4$—X—Y—$R^1$ or OCN—$R^1$, wherein $R^1$, X, Y and $Z^4$ and the meanings stated above, whereafter if $R^7$ stands for the benzyl radical this radical is removed by hydrogenolysis.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses β-adrenergic blocking activity, and furthermore this activity is cardioselective. This activity may be determined by the reversal of isoprenaline-induced tachycardia in rats or cats, a standard test for the determination of β-adrenergic blocking activity, and by relative freedom from antagonism of isoprenaline-induced vasodilation in cats or of the relief produced by isoprenaline of histamine-induced bronchospasm in guinea-pigs. Compounds exhibiting this cardioselective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is up to ten times more active as a cardioselective β-adrenergic blocking agent than practolol. At doses of an alkanolamine derivative of the invention which produce effective β-adrenergic blockade in rats or cats, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; α-adrenergic blocking agents, for example phentolamine and sympathomimetic bronchodilators, for example isoprenaline, orciprenaline, adrenaline and ephedrine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of 0.8 g. of β-isonicotinamidoethylamine and 0.75 g. of 2,3-epoxy-1-phenoxypropane is heated at 90° C. for 18 hours and then cooled and dissolved in 50 ml. of ethylacetate. The solution is added to a solution of 1.26 g. of oxalic acid in 50 ml. of ethylacetate, the mixture is filtered and the solid residue is crystallised from isopropanol. There is thus obtained 1-phenoxy-3-β-isonicotinamidoethylamino-2-propanol oxalate, m.p. 154°–156° C.

The β-isonicotinamidoethylamine used as starting material may be obtained as follows:

Ethyl isonicotinate hydrochloride (3.75 g.) is added portionwise to 5.4 g. of ethylenediamine at laboratory temperature. The mixture is allowed to stand for 30 minutes and then diluted with 50 ml. of water, and the mixture is extracted twice with 50 ml. of toluene each time. The combined toluene solutions are dried over anhydrous magnesium sulphate and evaporated to dryness under reduced pressure. The residue is dissolved in 25 ml. of methanol and ethereal hydrogen chloride solution is added. The mixture is filtered and the solid residue is extracted with 100 ml. of boiling methanol. The mixture is filtered and the combined methanol filtrate are evaporated to dryness under reduced pressure. The residue is crystallised from ethanol and there is thus obtained β-isonicotinamidoethylamine dihydrochloride, m.p. 263°–265° C. The free base is re-isolated by conventional means before use.

EXAMPLE 2

The process described in Example 1 is repeated except that 1.4 g. of β-2-thenamidoethylamine are used in place of the 0.8 g. of β-isonicotinamidoethylamine. There is thus obtained 1-phenoxy-3-(β-2-thenamidoethyl)-amino-2-propanol oxalate, m.p. 169°–171° C. after crystallisation from ethanol.

The β-2-thenamidoethylamine used as starting material may be prepared from ethyl 2-thenoate and ethylenediamine by a similar procedure to that described in the second part of Example 1, and is characterised as the oxalate salt, m.p. 175°–177° C. after crystallisation from ethanol.

EXAMPLE 3

The process described in Example 1 is repeated except that 1.54 g. of β-2-furamidoethylamine are used in place of the 0.8 g. of β-isonicotinamidoethylamine. There is thus obtained 1-phenoxy-3-(β-2-furamidoethyl)amino-2-propanol oxalate, m.p. 154°–156° C. after crystallisation from ethanol.

The β-2-furamidoethylamine used as starting material may be prepared from ethyl 2-furoate and ethylenediamine by a similar procedure to that described in the second part of Example 1, and is characterised as the hydrochloride, m.p. 155°–159° C. after crystallisation from ethanol.

EXAMPLE 4

A solution of 2.3 g. of p-acetamidobenzenesulphonyl chloride in 20 ml. of chloroform is added portionwise during 10 minutes to a solution of 3.0 g. of 1-β-(N-benzylamino)-ethylamino-3-phenoxy-2-propanol and 1 g. of triethylamine in 75 ml. of chloroform. The mixture is shaken, successively, with 60 ml. of aqueous 10% w/v sodium bicarbonate solution, 50 ml. of saturated brine and 50 ml. of water and the chloroform phase is then dried over anhydrous magnesium sulphate and evaporated to dryness under reduced pressure. The residue is dissolved in a mixture of 50 ml. of ethanol and 1 ml. of acetic acid and the solution is shaken in an atmosphere of hydrogen at laboratory temperature and atmospheric pressure in the presence of 0.3 g. of a 30% palladium-on-charcoal catalyst until 220 ml. of hydrogen have been absorbed. The mixture is filtered and the filtrate is evaporated to dryness under reduced pressure. The residue is diluted with 20 ml. of water and the mixture is neutralised with aqueous 10% w/v sodium bicarbonate solution and extracted three times with 20 ml. of ethyl acetate each time. The combined ethyl acetate extracts are dried over anhydrous magnesium sulphate and ethereal hydrogen chloride is added. The mixture is filtered and the solid residue is crystallised from 60 ml. of a 9:1 v/v mixture of ethanol and water. There is thus obtained 3-β-(p-acetamidobenzenesulphonamido)ethylamino-1-phenoxy-2-propanol hydrochloride, m.p. 231°–233° C.

EXAMPLE 5

A mixture of 2.2 g. of β-(p-acetamidobenzamido)ethylamine, 40 ml. of n-propanol and 1.5 g. of 1,2-epoxy-3-phenoxypropane is heated under reflux for 18 hours, cooled and filtered and the solid residue is crystallised from ethanol. There is thus obtained 3-β-(p-acetamidobenzamido)ethylamino-1-phenoxy-2-propanol, m.p. 157°–159° C.

EXAMPLE 6

The process described in Example 1 is repeated except that the appropriate 2,3-epoxy-1-phenoxypropane derivative and the appropriate heterocyclic β-amidoethylamine are used as starting materials. There are thus obtained the compounds described in the following table:

| R—OCH$_2$ . CHOH . CH$_2$NH—CH$_2$CH$_2$—NHCO—R$^1$ | | | | |
|---|---|---|---|---|
| R | R$^1$ | Base or salt | m.p. (°C.) | Crystallisation solvent |
| 2-cyanophenyl | 2-furyl | oxalate | 168–170 | ethanol |
| 2-cyanophenyl | 2-indolyl | hydrogen oxalate | 163–165 (d) | ethanol |
| 2-tolyl | 2-furyl | hydrogen oxalate | 183–184 | ethanol |
| 1-naphthyl | 2-furyl | hydrogen oxalate | 209–211 | aqueous ethanol |
| 3-tolyl | 2-furyl | hydrogen oxalate | 170–171 | ethanol |
| 2-allyloxyphenyl | 2-furyl | hydrogen oxalate hemihydrate | 123–125 | acetonitrile/methanol |
| 2-carbamoylphenyl | 2-thienyl | base | 189–190 | ethanol |

EXAMPLE 7

A mixture of 3.1 g. of 3-chloro-1-(2-iodophenoxy)-2-propanol, 1.9 g. of β-2-furamidoethylamine, 1.68 g. of sodium bicarbonate, 5 ml. of water and 40 ml. of n-propanol is heated under reflux for 18 hours, cooled, diluted with 50 ml. of water and extracted successively with 75 ml. and 25 ml. of ethyl acetate. The combined ethyl acetate extracts are dried and added to a solution of 1.26 g. of oxalic acid in 25 ml. of ethyl acetate. The mixture is filtered and the solid residue is crystallised from aqueous ethanol. There is thus obtained 3-(β-2-furamidoethyl)amino-1-(2-iodophenoxy)-2-propanol oxalate, m.p. 203°–204° C.

EXAMPLE 8

The process described in Example 5 is repeated except that the appropriate 1-aryloxy-2,3-epoxypropane and the appropriate β-amidoethylamine are used as starting materials. There are thus obtained the compounds described in the following table:

| R—OCH$_2$ . CHOH . CH$_2$NH—CH$_2$CH$_2$—NHCO—Y—R$^1$ | | | | |
|---|---|---|---|---|
| R | Y | R$^1$ | m.p. of Base | Crystallisation solvent |
| 2-cyanophenyl | — | 4-acetamidophenyl | 153–154 | ethanol |
| 2-cyanophenyl | —CH$_2$O— | 4-carbamoylmethylphenyl | 108–109 | isopropanol |
| 2-chloro- | —CH$_2$O— | 4-acetamido- | 95–98 | acetonitrile |
| phenyl | —CH$_2$— | phenyl | 125–128 | acetonitrile |
| 2-nitrophenyl | —CH$_2$— | 4-acetamidophenyl | 125–128 | acetonitrile |
| 2-methoxyphenyl | —CH$_2$— | 4-acetamidophenyl | 141–143 | acetonitrile |
| 2-chlorophenyl | —CH$_2$— | 4-acetamidophenyl | 128–131 | acetonitrile |

The β-(4-carbamoylmethylphenoxyacetamido)ethylamine used as starting material may be obtained as follows:

A mixture of 2.37 g. of ethyl 4-carbamoylmethylphenoxyacetate and 5 ml. of ethylenediamine is heated for 18 hours at 90° C. and then stirred with 50 ml. of water. The mixture is filtered and the filtrate is evaporated to dryness under reduced pressure. The residue is crystallised from isopropanol and there is thus obtained β-(4-carbamoylmethylphenoxyacetamido)ethylamine, m.p. 148°–150° C.

In a similar manner using 23.7 g. of ethyl 4-acetamidophenoxyacetate and 60 ml. of ethylenediamine as starting materials there is obtained β-(4-acetamidophenoxyacetamido)ethylamine, m.p. 210°–212° C.

EXAMPLE 9

A mixture of 2.0 g. of β-isobutyramidoethylamine, 3.0 g. of 2,3-epoxy-1-(4-indolyloxy)propane and 50 ml. of isopropanol is heated at 90° C. for 18 hours and is then evaporated to dryness under reduced pressure. The residue is dissolved in 30 ml. of acetonitrile, the mixture is filtered and the filtrate is added to a solution of 2.52 g. of oxalic acid in 25 ml. of acetonitrile. The mixture is cooled and filtered, the filtrate is evaporated to dryness under reduced pressure and the residue is triturated twice with 25 ml. of ethanol each time. The mixture is filtered and there is thus obtained as solid residue 1-(4-indolyloxy)-3-β-isobutyramidoethylamino-2-propanol hydrogen oxalate, m.p. 168°–171° C.

The process described above is repeated except that the appropriate 1-substituted-2,3-epoxypropane and the appropriate β-amidoethylamine are used as starting materials. There are thus obtained the compounds described in the following table:

| R—OCH$_2$ . CHOH . CH$_2$NH—CH$_2$CH$_2$—NHCO—Y—R$^1$ | | | | | |
|---|---|---|---|---|---|
| R | Y | R$^1$ | Base or salt | m.p.(°C.) | Crystallisation solvent |
| Benzodioxan- | — | isopropyl | base | 118–120 | toluene/ |

-continued

| | | | | | |
|---|---|---|---|---|---|
| R | Y | R¹ | Base or salt | m.p.(°C.) | Crystallisation solvent |
| 5-yl | | | | | petroleum ether (b.p 40-60° C.) |
| Benzodioxan-5-yl | —CH₂— | phenyl | hydrogen oxalate | 114-116 | toluene |
| Benzodioxan-5-yl | —NH— | phenyl | base | 153-154 | ethanol |
| Benzodioxan-5-yl | — | 2-thienyl | hydrogen oxalate | 165-167 | methanol |
| Benzodioxan-5-yl | —CH₂O— | 2-allyl-phenyl | hydrogen oxalate | 87-90 | ethyl acetate |
| Benzo[b]-thien-4-yl | —NH— | phenyl | hydrogen oxalate | 186-188 | ethanol |
| Benzofuran-4-yl | —NH— | phenyl | hydrogen oxalate | 188-190 | ethanol |
| 4-Oxochroman-8-yl | —NH— | phenyl | hydrogen oxalate | 184 (d) | ethanol |
| Thiazol-2-yl | — | isopropyl | hydrogen oxalate | 158-160 (d) | aqueous ethanol |

R—OCH₂ . CHOH . CH₂NH—CH₂CH₂—NHCO—Y—R¹

EXAMPLE 10

A mixture of 2.08 g. of 2,3-epoxy-1-(benzodioxan-5-yloxy)propane, 1.92 g. of 1-methyl-2-phenylacetamidoethylamine and 50 ml. of isopropanol is heated under reflux for 4 hours, and is then evaporated to dryness under reduced pressure. The residue is dissolved in 50 ml. of ethyl acetate and the solution is extracted twice with 50 ml. of water each time. The ethyl acetate solution is dried and evaporated to dryness under reduced pressure and the residue is crystallised from toluene. There is thus obtained 1-(benzodioxan-5-yloxy)-3-(1-methyl-2-phenylacetamidoethyl)amino-2-propanol, m.p. 93°-94° C.

EXAMPLE 11

A mixture of 2.08 g. of 2,3-epoxy-1-(benzodioxan-5-yloxy)propane, 1.44 g. of γ-isobutyramidopropylamine and 50 ml. of isopropanol is heated under reflux for 4 hours and is then evaporated to dryness under reduced pressure. The residue is dissolved in 50 ml. of ethyl acetate and the solution is extracted twice with 50 ml. of water each time. The ethyl acetate phase is separated, dried and added to a solution of 1.26 g. of oxalic acid in 30 ml. of acetone. The mixture is filtered and the solid residue is crystallised from acetonitrile. There is thus obtained 1-(benzodioxan-5-yloxy)-3-γ-isobutyramidopropylamino-2-propanol hydrogen oxalate, m.p. 122°-125° C.

EXAMPLE 12

A mixture of 2.43 g. of 3-(2,3-epoxypropoxy)-4-morpholino-1,2,5-thiadiazole, 1.3 g. of β-isobutyramidoethylamine and 50 ml. of isopropanol is heated at 90° C. for 18 hours and is then evaporated to dryness under reduced pressure. The residue is stirred with 100 ml. of aqueous 2N-hydrochloric acid and the mixture is extracted three times with 50 ml. of ethyl acetate each time. The aqueous acidic phase is separated, basified with aqueous 11N-sodium hydroxide solution and extracted three times with 75 ml. of ethyl acetate each time. The combined ethyl acetate extracts are dried over anhydrous magnesium sulphate and evaporated to dryness under reduced pressure, and the residue is dissolved in 25 ml. of acetone. The solution is added to a solution of 2.5 g. of oxalic acid in 25 ml. of acetone, the mixture is filtered and the solid residue is washed with acetone and crystallised from ethanol. There is thus obtained 3-β-isobutyramidoethylamino-1-(4-morpholino-1,2,5-thiadiazol-3-yloxy)-2-propanol hydrogen oxalate, m.p. 194°-196° C. (with decomposition).

EXAMPLE 13

A mixture of 3.1 g. of 1-chloro-3-β-isobutyramidoethylamino-2-propanol hydrogen oxalate, 1.5 g. of 4-hydroxybenzo[b]thiophene, 1.4 g. of sodium hydroxide, 5 ml. of water and 50 ml. of isopropanol is heated under reflux for 18 hours and is then evaporated to dryness under reduced pressure. The residue is stirred with 100 ml. of water and the mixture is extracted twice with 50 ml. of chloroform each time. The combined chloroform extracts are dried and evaporated to dryness under reduced pressure and the residue is crystallised from ethyl acetate. There is thus obtained 1-(benzo[b]thien-4-yl)-3-β-isobutyramidoethylamino-2-propanol, m.p. 121°-123° C.

EXAMPLE 14

A mixture of ethyl 2-p-chlorophenylthiazol-4-yl-acetate and 2.52 g. of 3-β-aminoethylamino-1-(2-cyanophenoxy)-2-propanol is heated at 90° C. for 18 hours and is then dissolved in 25 ml. of hot acetonitrile. The solution is cooled and filtered and the solid residue is crystallised from ethanol. There is thus obtained 1-(2-cyanophenoxy)-3-β-(2-p-chlorophenylthiazol-4-ylacetamido)ethylamino-2-propanol, m.p. 113°-114° C.

The process described above is repeated except that the appropriate ethyl ester is used as starting material and, in one case, the corresponding 2-chlorophenoxy derivative is used. There are thus obtained the compounds described in the following table:

R—OCH₂ . CHOH . CH₂NH—CH₂CH₂—NHCO—Y—R¹

| R | Y | R¹ | Base or salt | m.p.(°C.) | Crystallisation solvent |
|---|---|---|---|---|---|
| 2-cyano- | —CH₂— | 3-indolyl | oxalate | 200-202 | aqueous ethanol |

-continued

R—OCH₂ . CHOH . CH₂NH—CH₂CH₂—NHCO—Y—R¹

| R | Y | R¹ | Base or salt | m.p.(°C.) | Crystallisation solvent |
|---|---|---|---|---|---|
| phenyl 2-cyano-phenyl | —CH₂— | 3-thienyl | base | 159–160 | ethanol |
| 2-cyano-phenyl | —CH₂— | 1,4-dihydro-6-methoxy-4-oxoquino-lin-2-yl | base | 171–173 | methanol |
| 2-cyano-phenyl | —CH₂— | 2-p-chloro-phenyl-6-methoxy-pyrimidin-4-yl | oxalate | 195–197 | aqueous methanol |
| 2-chloro-phenyl | —CH₂— | 2-benzimi-dazolyl | bis hydrogen oxalate | 163–165 | methanol |
| 2-cyano-phenyl | — | 5-methyl-pyrazol-3-yl | base | 160–161 | ethanol |

EXAMPLE 15

A mixture of 0.84 g. of 3-β-aminoethylamino-1-(2-cyanophenoxy)-2-propanol and 0.88 g. of ethyl 4-acetamidomethylphenoxyacetate is heated at 90° C. for 2 hours, and is then dissolved in 25 ml. of hot acetonitrile. The mixture is filtered, the solid being discarded, and the filtrate is cooled and then refiltered. The solid residue is crystallised from acetonitrile and there is thus obtained 3-β-(4-acetamidomethylphenoxyacetamido)ethylamino-1-(2-cyanophenoxy)-2-propanol, m.p. 98°–100° C.

In a similar manner using 1.2 g. of 3-(β-aminoethylamino)-1-(2-cyanophenoxy)-2-propanol and 1.29 of ethyl 4-methanesulphonamidophenylacetate as starting materials there is obtained 1-(2-cyanophenoxy)-3-β-(4-methanesulphonamidophenylacetamido)ethylamino-2-propanol, isolated as its oxalate, m.p. 180°–182° C. after crystallisation from isopropanol.

In a similar manner using 2.36 g. of 3-(β-aminoethylamino)-1-(2-cyanophenoxy)-2-propanol and 2.37 g. of ethyl 4-carbamoylmethoxyphenylacetate as starting materials there is obtained 3-β-(4-carbamoylmethoxyphenylacetamido)ethylamino-1-(2-cyanophenoxy)-2-propanol, isolated as its hydrogen oxalate, m.p. 123°–125° C. after crystallisation from ethyl acetate.

The ethyl 4-acetamidomethylphenoxyacetate used as starting material in the first part of this Example may be obtained as follows:

A mixture of 2.5 g. of 4-acetamidomethylphenol, 15 ml. of acetone, 2.1 g. of potassium carbonate and 1.8 ml. of ethyl bromoacetate is heated under reflux for 18 hours and is then filtered and the filtrate is evaporated to dryness under reduced pressure. The residue is dissolved in 30 ml. of ethyl acetate and the solution is washed twice with 25 ml. of water each time, dried and evaporated to dryness under reduced pressure. The residue is crystallised from toluene and there is thus obtained ethyl 4-acetamidomethylphenoxyacetate, m.p. 85°–86° C.

EXAMPLE 16

A mixture of 2.68 g. of 3-β-aminoethylamino-1-(benzodioxan-5-yloxy)-2-propanol and 2.25 g. of ethyl p-nitrophenoxyacetate is heated at 90° C. for 18 hours and is then dissolved in 50 ml. of ethyl acetate. The solution is washed twice with 50 ml. of water each time and then dried and added to a solution of 1.26 g. of oxalic acid in 50 ml. of ethyl acetate. The mixture is filtered and the solid residue is heated under reflux with 50 ml. of acetonitrile. The solution is cooled and filtered and the solid residue is crystallised from ethanol. There is thus obtained 1-(benzodioxan-5-yloxy)-3-β-(p-nitrophenoxyacetamido)ethylamino-2-propanol hydrogen oxalate, m.p. 162°–164° C.

The process described above is repeated except that the ethyl p-nitrophenoxyacetate is replaced by either ethyl p-acetylphenoxyacetate or ethyl p-(3-methylureidophenyl)acetate, and that in one case the product is isolated as the hydrochloride and in the other case the product is isolated as the free base. There are thus obtained respectively 1-(benzodioxan-5-yloxy)-3-β-(p-acetylphenoxyacetamido)ethylamino-2-propanol hydrochloride hydrate, m.p. 129°–131° C. after crystallisation from ethanol, and 1-(benzodioxan-5-yloxy)-3-β-(p-3-methylureidophenylacetamido)ethylamino-2-propanol, m.p. 115°–117° C. after crystallisation from acetonitrile.

The 3-(β-aminoethylamino)-1-(benzodioxan-5-yloxy)-2-propanol used as staring material may be obtained as follows:

A mixture of 20.8 g. of 1-(benzodioxan-5-yloxy)-2,3-epoxypropane and 120 g. of ethylenediamine is heated at 90° C. for 18 hours and is then evaporated to dryness under reduced pressure. The residue is stirred with 100 ml. of water and the mixture is extracted four times with 100 ml. of chloroform each time. The combined chloroform extracts are dried and evaporated to dryness under reduced pressure and there is thus obtained as residue 3-β-aminoethylamino-1-(benzodioxan-5-yloxy)-2-propanol.

EXAMPLE 17

A mixture of 0.86 g. of quinoline-2-carboxylic acid, 50 ml. of ethyl acetate, 1.1 g. of 2,4,5-trichlorophenol and 1.25 g. of N,N-dicyclohexylcarbodi-imide is stirred at laboratory temperature for 2 hours and then filtered, and the filtrate is added to a solution of 1.17 g. of 3-β-aminoethylamino-1-(2-cyanophenoxy)propanol in 30 ml. of acetonitrile. The mixture is stirred at laboratory temperature for 18 hours and is then extracted twice with 50 ml. of aqueous 105 v/v acetic acid solution each time. The combined extracts are basified with aqueous 11N-sodium hydroxide solution and the mixture is extracted twice with 30 ml. of ethyl acetate each time. The combined extracts are dried and evaporated to dryness under reduced pressure, the residue is dissolved in 20 ml. of acetonitrile, and the solution is added to a solution of 0.63 g. of oxalic acid in 20 ml. of acetonitrile. The mixture is filtered and the solid residue is crystallised from water. There is thus obtained 1-(2-cyanophenoxy)-3-β-(quinoline-2-carboxamido)ethylamino-2-propanol hydrogen oxalate, m.p. 179°–181° C.

EXAMPLE 18

1.6 g. of 1-(benzodioxan-5-yloxy)-3-β-(p-nitrophenoxyacetamido)ethylamino-2-propanol hydrogen oxalate (Example 16) is converted to its free-base form by conventional methods and the base is dissolved in 50 ml. of ethanol. 200 Mg. of a 30% palladium-on-charcoal catalyst are added and the mixture is shaken with hydrogen at laboratory temperature and atmospheric pressure until 230 ml. of hydrogen have been absorbed. The mixture is filtered and the filtrate is evaporated to dryness under reduced pressure. The residue is dissolved in 30 ml. of acetonitrile and an excess of a saturated ethereal hydrogen chloride solution is added. The mixture is filtered and the solid residue is crystallised from 20 ml. of ethanol. There is thus obtained 3-β-(p-aminophenoxyacetamido)ethylamino-1-(benzodioxan-5-yloxy)-2-propanol dihydrochloride, m.p. 200°–202° C.

EXAMPLE 19

A mixture of 1.7 g. of 3-β-(p-benzyloxyphenoxyacetamido)ethylamino-1-(benzodioxan-5-yloxy)-2-propanol oxalate (m.p. 187°–189° C.; prepared by a similar process to that described in Example 9), 0.2 g. of a 30% palladium-on-charcoal catalyst and 40 ml. of acetic acid is shaken with hydrogen at laboratory temperature and atmospheric pressure until 125 ml. of hydrogen have been absorbed. 40 Ml. of water are then added and the mixture is filtered. The filtrate is evaporated to dryness under reduced pressure, the residue is dissolved in 30 ml. of acetonitrile and the solution obtained is added to a solution of 0.42 g. of oxalic acid in 30 ml. of acetonitrile. The mixture is filtered and the solid residue is crystallised from ethanol. There is thus obtained 1-(benzodioxan-5-yloxy)-3-β-(p-hydroxyphenoxyacetamido)ethylamino-2-propanol hydrogen oxalate, m.p. 188°–190° C.

The process described above is repeated except that 1-(2-benzyloxyphenoxy)-3-(β-2-furamidoethyl)amino-2-propanol (m.p. 84°–85° C.; prepared by a similar process to that described in Example 6) is used as starting material. There is thus obtained 1-(2-hydroxyphenoxy)-3-(β-2-furamidoethyl)amino-2-propanol hydrogen oxalate, m.p. 176°–178° C. after crystallisation from water.

EXAMPLE 20

A solution of phenyl isocyanate (0.6 g.) in acetonitrile (10 ml.) is added during 5 minutes to a stirred solution of 1-(benzodioxan-5-yloxy)-3-β-aminoethylamino-2-propanol 1.34 g.) in acetonitrile (50 ml.) which is maintained at −30° C., and the mixture is then allowed to warm up to room temperature and is filtered. The solid residue is crystallised from ethanol and there is thus obtained 1-(benzodioxan-5-yloxy)-3-β-(3-phenylureido)ethylamino-2-propanol, m.p. 154°–155° C.

What we claim is:

1. An alkanolamine derivative selected from a compound of the formula:

R.OCH₂.CHOH.CH₂NH—A—NH—X—Y—R¹ wherein A is alkylene of from 2 to 12 carbon atoms; wherein X is sulphonyl (—SO₂—); wherein Y is a direct link, or is alkylene or alkyleneoxy each of up to 6 carbon atoms; and wherein R is aryl of the formula:

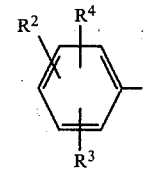

and R¹ is aryl of the formula:

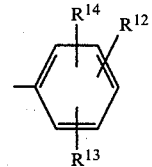

wherein R², R³, R¹² and R¹³, which may be the same or different, each is hydrogen, halogen, hydroxy, amino, nitro or cyano, or alkyl, hydroxyalkyl, cycloalkyl, alkenyl, alkynyl, alkoxy, alkylthio, cycloalkoxy, alkenyloxy, alkynyloxy or alkanoyl each of up to 6 carbon atoms or aryl, aryloxy or dialkylamino each of up to 12 carbon atoms; or wherein R² and R³ together, and/or R¹² and R¹³ together, form trimethylene, tetramethylene, 1-oxotetramethylene, propenylene, but-2-enylene or buta-1,3-dienylene such that together with the adjacent benzene ring they form respectively indanyl, 5,6,7,8-tetrahydronaphthyl, 5-oxo-5,6,7,8-tetrahydronaphthyl, indenyl, 5,8-dihydronaphthyl or naphthyl; wherein R⁴ is hydrogen or amidic of the formula:

R¹⁵R¹⁶N—CO—Q—

R¹⁵R¹⁶N—CO—NH—Q—

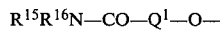
R¹⁵R¹⁶N—CO—Q¹—O—

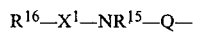
R¹⁶—X¹—NR¹⁵—Q— or
wherein X¹ is carbonyl or sulphonyl, wherein Q is a direct link or is alkylene or alkenylene each of up to 6 carbon atoms; wherein Q¹ is alkylene of up to 6 carbon atoms; wherein R¹⁵ is hydrogen or alkyl of up to 6 carbon atoms; wherein R¹⁶ is hydrogen or alkenyl, cycloalkyl, hydroxyalkyl or alkoxyalkyl each of up to 6 carbon atoms, or alkyl, aryl, aralkyl or aralkenyl each of up to 10 carbon atoms; and where R¹⁴ is amidic as defined above for R⁴; and an acid-addition salt thereof.

2. An alkanolamine derivative as claimed in claim 1 selected from a compound of the formula given in claim 1 wherein A is ethylene, 1-methylethylene or 1,1-dimethylethylene, wherein X is sulphonyl, wherein Y is a direct link or is methylene or methyleneoxy or imino, and wherein R is aryl of the formula:

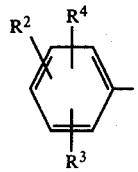

and $R^1$ is aryl of the formula:

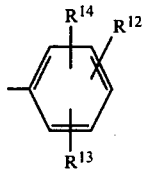

wherein $R^2$, $R^3$, $R^{12}$ and $R^{13}$, which may be the same or different, each is hydrogen, fluorine, chlorine, bromine, iodine, hydroxy, amino, nitro, cyano, methyl, ethyl, n-propyl, hydroxymethyl, 1-hydroxyethyl, cyclopropyl, cyclopentyl, allyl, ethynyl, methoxy, isopropoxy, methylthio, cyclopentyloxy, allyloxy, propargyloxy, formyl, acetyl, phenyl, phenoxy or dimethylamino, or wherein $R^2$ and $R^3$ together, and/or $R^{12}$ and $R^{13}$ together, are trimethylene, tetramethylene, 1-oxotetramethylene, propenylene, but-2-enylene or buta-1,3-dienylene; wherein $R^4$ is hydrogen, acetamido, propionamido, methanesulphonamido, carbamoyl, carbamoylmethyl, acetamidomethyl, 3-methylureido, carbamoylmethoxy, 3-n-butylureido, N-methylcarbamoylmethoxy or N-$\beta$-hydroxyethylcarbamoylmethoxy and wherein $R^{14}$ is, other than hydrogen, as defined above for $R^4$; and an acid-addition salt thereof.

3. An alkanolamine derivative as claimed in claim 1 selected from a compound of the formula given in claim 1 wherein A is ethylene, 1-methylethylene or 1,1-dimethylethylene, wherein R and $R^1$ are both aryl, wherein $R^2$ is hydrogen, chloro, cyano, nitro or methoxy which is in the 2-position of the aryl nucleus, wherein $R^3$, $R^4$, $R^{12}$ and $R^{13}$ are all hydrogen, wherein $R^{14}$ has the formula:

$R^{16}NHCO—Q—$ $R^{16}NHCONH—$ $R^{16}NHCO—Q^1—O—$ $R^{16}—X^1—NH—Q—$ or wherein $X^1$ is carbonyl or sulphonyl, wherein $R^{16}$ is hydrogen or methyl, wherein Q is a direct link or is methylene and wherein $Q^1$ is methylene, which substituent $R^{14}$ is in the 4-position of the aryl nucleus, wherein X is sulphonyl and wherein Y is a direct link or is methylene or methyleneoxy, and an acid-addition salt thereof.

4. A compound selected from 1-phenoxy-3-$\beta$-(p-acetamidobenzenesulphonamido)ethylamino-2-propanol; an acid-addition salt thereof.

5. An acid-addition salt as claimed in claim 1 which is a hydrochloride, hydrobromide, phosphate, sulphate, oxalate, lactate, tartrate, acetate, salicylate, citrate, benzoate, $\beta$-naphthoate, adipate or 1,1-methylene-bis-(2-hydroxy-3-naphthoate), or a salt derived from a sulphonated polystyrene resin.

6. A pharmaceutical composition comprising as active ingredient at least one alkanolamine derivative or an acid-addition salt thereof, claimed in claim 1, in association with a pharmaceutically-acceptable diluent or carrier therefor.

7. A composition as claimed in claim 6 which contains, in addition to the alkanolamine derivative, one or more drugs selected from sedatives, vasodilators, diuretics, hypotensive agents, cardiac membrane stabilising agents, agents used in the treatment of Parkinson's disease and other tremors, cardiotonic agents, $\alpha$-adrenergic blocking agents and sympathomimetic bronchodilators.

8. A method for the treatment or prophylaxis of heart diseases and hypertension in a warm-blooded animal which comprises administering to said animal an effective amount of at least one compound claimed in claim 1.

9. A method for producing coronary $\beta$-adrenergic blockade in a warm-blooded animal in need of such blockade which comprises administering to said animal an effective amount of at least one compound claimed in claim 1.

* * * * *